United States Patent
Brugger et al.

(10) Patent No.: US 11,857,766 B2
(45) Date of Patent: Jan. 2, 2024

(54) DEVICE AND METHOD FOR CLOSING SYRINGE BODIES

(71) Applicants: Stefan Brugger, Burgrieden/Rot (DE); Margit Klotz, Laupheim (DE)

(72) Inventors: Stefan Brugger, Burgrieden/Rot (DE); Margit Klotz, Laupheim (DE)

( * ) Notice: Subject to any disclaimer, the term of this patent is extended or adjusted under 35 U.S.C. 154(b) by 0 days.

(21) Appl. No.: 17/696,346

(22) Filed: Mar. 16, 2022

(65) Prior Publication Data
US 2022/0313911 A1 Oct. 6, 2022

Related U.S. Application Data

(63) Continuation of application No. PCT/EP2020/075711, filed on Sep. 15, 2020.

(30) Foreign Application Priority Data
Sep. 16, 2019 (DE) .......................... 102019214071.8

(51) Int. Cl.
*A61M 5/178* (2006.01)
*A61M 5/00* (2006.01)

(52) U.S. Cl.
CPC .......... *A61M 5/1782* (2013.01); *A61M 5/008* (2013.01); *A61M 2205/19* (2013.01); *A61M 2209/045* (2013.01); *A61M 2209/084* (2013.01)

(58) Field of Classification Search
CPC .......... A61M 2205/19; A61M 2207/10; A61M 2209/045; A61M 2209/084; A61M 2039/2486; A61M 5/28; A61M 5/178; A61M 5/135

USPC ......................................................... 53/489
See application file for complete search history.

(56) References Cited

U.S. PATENT DOCUMENTS

| 1,990,301 | A | | 2/1935 | Mora | |
|---|---|---|---|---|---|
| 3,737,973 | A | * | 6/1973 | Stawski | B65B 3/006 29/451 |
| 5,519,984 | A | * | 5/1996 | Beussink | B65B 7/2821 53/489 |
| 10,266,293 | B1 | * | 4/2019 | Russell | B65B 31/027 |
| 11,202,864 | B2 | * | 12/2021 | Stetzer | A61M 5/31505 |
| 11,254,901 | B2 | * | 2/2022 | Langenfeld | C12M 1/26 |
| 11,540,975 | B2 | * | 1/2023 | Kloke | B65B 3/003 |

(Continued)

FOREIGN PATENT DOCUMENTS

| CN | 110446512 A | * | 11/2019 | ............ A61M 5/008 |
|---|---|---|---|---|
| KR | 101617853 | | 5/2016 | |

OTHER PUBLICATIONS

International Search Report; PCT, Form PCT/ISA/210; dated Jan. 11, 2021.

*Primary Examiner* — Timothy L Maust
(74) *Attorney, Agent, or Firm* — Pitts Lake, LLC (57) ABSTRACT

The invention relates to a device (IO) for manually inserting a plunger-type stopper into a syringe cylinder, comprising a receptacle (18) designed to hold the syringe cylinder; a tubular barrel (30) designed to accommodate the plunger-type stopper in its interior, a holding device (28) designed to hold the barrel, and a moving device (40, 42, 44, 46, 48) designed to move the plunger-type stopper; the holding device (28) having an actuation portion (34) for moving the barrel (30) relative to the plunger-type stopper. The present invention further relates to a corresponding method.

10 Claims, 1 Drawing Sheet

(56) References Cited

U.S. PATENT DOCUMENTS

| | | | |
|---|---|---|---|
| 2006/0168916 A1* | 8/2006 | Griebel | B65B 3/003 53/489 |
| 2015/0190578 A1* | 7/2015 | Okihara | B65B 7/2821 53/111 R |
| 2022/0062557 A1* | 3/2022 | Wallaert | A61M 5/002 |

* cited by examiner

FIG. 1

DEVICE AND METHOD FOR CLOSING SYRINGE BODIES

CROSS-REFERENCE TO RELATED APPLICATIONS

This application is a continuation of international application number PCT/EP2020/075711 filed on Sep. 15, 2020.

FIELD OF INVENTION

The present invention relates to a device for manually inserting a plunger-type stopper made of elastomer, which forms part of a plunger, into a syringe cylinder.

BACKGROUND

The methods used to date for closing syringes with plunger-type stoppers are either very complex (use of filling machines) or not sterile or representative (manipulation of the plunger-type stopper during setting to avoid excess pressure). In an early phase of development or during a life cycle management of a liquid drug or medical device whose dosage form is to be a syringe, there are basically two reasons which make it necessary to close syringes with plunger-type stoppers outside a routine large-scale production:

There is a need to investigate and analyze the material compatibility with regard to the interaction between solution and packaging material over a longer period of time (if possible corresponding to the intended shelf life of the drug) and, if necessary, to adapt the formulation or the packaging material. Here, it is essential that the method of production corresponds as closely as possible to a later industrial production with a filling machine. Even minor deviations can have such a massive influence on the analysis results that it is no longer possible to make a reliable statement about compatibility. This can lead to considerable problems in later phases of the development of a drug (reduction of shelf life) or even to a new development of the formulation/packaging material, which causes considerable expenditure of time and money;

Toxicological studies as well as in vivo tests are often required in the early stages of drug development. For these tests, the targeted sterile drugs must also exhibit actual sterility. Since this cannot be guaranteed by manipulating the plunger-type stoppers during conventional manual stoppering, this type of production cannot be used. Filling on a filling machine is equally difficult, as GMP regulations do not allow substances with unknown toxicological properties to be introduced into the premises here (avoidance of cross-contamination, cleaning validation not possible). In addition, the batch size available for automated filling on a filling machine is often insufficient (dead volumes).

There was therefore a need to provide a device or method that would enable the above-mentioned filling of syringes even in very small batches.

BRIEF DESCRIPTION OF THE DRAWINGS

In the following, the present invention will be described in greater detail with reference to the accompanying drawings by way of an exemplary embodiment, wherein.

DESCRIPTION

In a first aspect of the present invention, this problem is solved by a device for manually inserting a plunger-type stopper made of elastomer, which forms part of a plunger, into a syringe cylinder, comprising: a receptacle adapted to hold the syringe cylinder; a tubular barrel adapted to receive the plunger-type stopper therein; a holding device adapted to hold the barrel relative to the receptacle; and a moving device adapted to move the plunger-type stopper relative to the barrel; wherein the holding device comprises an actuation portion adapted to be manually actuated to displace the barrel relative to the plunger-type stopper.

The device according to the invention enables a series of filled syringes (and other syringe-like cylindrical tubes such as cartridges, double-chamber cartridges, and double-chamber syringes) to be used from the quantity of 1. In addition, the device according to the invention can be used to fill a respective syringe aseptically and perfectly for different applications. This leads to a significant reduction in costs and time for the applications described so far.

In particular, the device according to the invention allows a filling sequence of fully automated filling machines to be imitated, so that a later changeover from the small series to the actual series of drug production is possible without major conversions in this context, components of a filling machine can also be taken directly for the device according to the invention in order to achieve absolutely identical conditions for the properties of the syringe produced. For example, the barrel and plunger (see below) come into question here.

By means of the device according to the invention, a respective plunger-type stopper can be set without the formation of excess pressure in the syringe cylinder, as a result of which, for example, product could be expelled unintentionally. In connection with the present invention, therefore, the term "pressure-free" stopper setting is also used.

The plunger-type stoppers can thus be positioned with absolute precision, so that a desired and required "headspace" and uniformity can be obtained over an entire batch.

Inert gases or other gases can be connected for settling gassing. In general, the device according to the invention can also be used and operated in an aseptic environment (from laboratory to isolator) along the entire development chain (formulation development, stability studies, toxicity studies, clinical studies, packaging change to life cycle management).

Advantageously, at least all components which come into contact with parts of the syringe to be filled and/or the drug, in particular all components, of the device according to the invention are autoclavable.

Furthermore, it can be advantageous that at least the holder and/or the barrel is/are designed in such a way that it/they can be replaced by a counterpart for a syringe of a different format. In this way it can be achieved, for example, that syringes of the formats 1 ml, 3 ml or 10 ml can be filled.

In the device according to the invention, for example, an already filled syringe cylinder can first be arranged in the receptacle, then the syringe cylinder is displaced relative to the barrel in such a way that the end of the barrel associated with the drug is at a predetermined distance from the drug. Now, a plunger-type stopper can be displaced through the barrel, wherein gas disposed in the barrel between the plunger-type stopper and the drug can be expelled upon displacement of the plunger-type stopper in the barrel and can escape from the syringe cylinder between the barrel and the syringe cylinder without causing an overpressure to form in the syringe cylinder. When the plunger-type stopper is located at the end of the barrel adjacent to the drug, an operator of the device according to the invention actuates the actuation portion, thereby displacing the barrel relative to the plunger-type stopper and away from the drug. As this occurs, the plunger-type stopper expands such that it interacts with the syringe cylinder in a sealing manner. The finished syringe can now be removed from the device according to the invention.

In a further development of the present invention, the actuation portion of the holding device may comprise a rocking device adapted to transfer a manual actuating force acting in a first direction, which has been input at a first end of the rocking device, to a lever force acting in a second direction at a second end of the rocking device arranged opposite to the first end, wherein the first direction may be substantially opposite to the second direction. Such a device may allow a small actuating force at one end to be converted into a comparatively larger displacement force at the other end, so that actuation of the actuation portion may be simplified.

The rocking device can be designed as an elongated plate-like element. This can be a particularly simple and cost-effective design of the rocking device.

Furthermore, the plate-like element may thereby have a first end adapted to be actuated by a finger and a second end arranged substantially opposite to the first end and which at least partially encloses the barrel. The plate-like element may therefore be arranged on the device according to the invention, in particular in such a way that it is readily accessible to a user so that the user can act on the first end of the plate-like element with his finger.

Advantageously, the device may further comprise at least one support element to which the holding device and/or the displacement device are/is connected.

Also, the device may further comprise a base plate which may advantageously be connected to the at least one support element. The at least one support element and the base plate can thus together form a frame on which the above-described parts of the device according to the invention can be supported.

In particular, the receptacle can be attached to the base plate. In this way, the receptacle can be supported relative to the base plate and, for example, horizontal play of the receptacle relative to the base plate can be reduced or even avoided.

The receptacle can be adjustable relative to the holding device and/or the displacement device, advantageously via at least one screw connection. This allows the syringe cylinder to be displaced in the device. Furthermore, the device according to the invention can thus be adapted to the filling of syringes with mutually different filling levels or different syringe formats.

Advantageously, the holding device and/or the displacement device and/or the receptacle can be adjustable relative to one another, advantageously via at least one screw connection in each case. In this way, maximum flexibility can be achieved when producing the syringes and/or when adapting the device according to the invention to different syringe formats and/or filling levels.

The barrel may further be adapted to be displaceable relative to the receptacle such that, in a predetermined position of its displacement path, it projects at least partially into an interior of a syringe cylinder arranged on the receptacle. Thus, the barrel with a plunger-type stopper arranged therein can be displaced into the syringe cylinder until the barrel is in the vicinity of a drug arranged in the syringe cylinder.

In particular, the barrel can have a radially outwardly extending collar at one end. The barrel can thus be inserted into a corresponding holder, for example from above, and held in place due to the collar and the force of gravity. This may allow easy interchangeability of the barrel on the device according to the invention.

Further, the receptacle configured to hold the syringe cylinder may include at least two parts.

In this regard, the receptacle may include a first centering receptacle configured to hold a second centering receptacle and the second centering receptacle configured to hold the syringe cylinder, wherein the second centering receptacle is at least partially immersed in the first centering receptacle.

The first centering receptacle may have a depth stop configured to limit the displacement path of the second centering receptacle. In other words, the displacement path of the second centering receptacle can be defined by the first centering receptacle.

At its end essentially opposite the first centering receptacle, the second centering receptacle can have a holder for a syringe cylinder, which is advantageously designed in the shape of a hollow cylinder or in the form of a clamp. A respective syringe cylinder can then be inserted into this holder of the second centering receptacle either from above or engaged laterally, for example in a horizontal direction, if the receptacle is designed, for example, as an elastic clamp. At this point, the drug can already be present in the syringe cylinder or can only be filled into the holder of the second centering receptacle after the latter has been adjusted.

Furthermore, the holding device set up to hold the barrel can at least partially enclose the barrel. In particular, partial enclosure can be such that the barrel is only accommodated in such a way that it can be displaced along its longitudinal extension.

In this context, the holding device can be hollow-cylindrical in shape with a bore, preferably concentric with the center axis of the holding device, for receiving the barrel.

In a further development of the present invention, the displacement device arranged for displacing the plunger-type stopper relative to the barrel may comprise a plunger guide arranged for aligning a plunger relative to the barrel, and the plunger arranged for displacing the plunger-type stopper relative to the barrel. The plunger can be designed here, for example, as a rod which can be displaced in particular parallel, advantageously coaxially, to a longitudinal center axis of the syringe cylinder.

In this context, the displacement device can further comprise a plunger guide receptacle which is set up to hold the plunger guide. For example, the plunger guide can be designed as a slide bushing.

Furthermore, the plunger guide or the plunger guide receptacle can be connected to the at least one support element, wherein the plunger guide can advantageously be directly or indirectly adjustable, advantageously via at least one screw connection. Again, divisibility of the plunger guide may allow the device according to the invention to be adapted to different syringe formats.

Advantageously, the plunger can have a cylindrical section at the end facing the holding device, the outer diameter of which is smaller than a clear inner diameter of the barrel. This can allow the plunger to be inserted into the barrel in order to move the plunger-type stopper through the tube. An only slightly smaller diameter of this section of the plunger compared to the internal diameter of the barrel can prevent unintentional tilting of the plunger-type stopper in the barrel.

The plunger may further comprise, at the end opposite the holding device, an advantageously radially outwardly extending head which is advantageously adapted to be manually actuated, advantageously with a finger, to displace the plunger-type stopper relative to the barrel. On the one hand, the head of the plunger may provide a sufficiently large actuation surface to allow an operator to manually displace the plunger. On the other hand, the head of the plunger may also serve as a weight to assist the operator in applying the force necessary to displace the plunger-type stopper through the barrel.

In particular, the plunger may further comprise an advantageously adjustable depth stop adapted to define the end of the displacement path of the plunger-type stopper in the barrel by the displacement device. This can allow an operator, after the depth stop has been successfully adjusted and the syringe format/fill level remains the same, to displace the plunger to the limit without having to pay attention to the position of the plunger relative to the syringe cylinder. Once the plunger has reached its maximum displacement distance, the operator can actuate the actuation section, such as the rocking device, which releases the plunger-type stopper as described above.

Further, the device may comprise a securing means adapted to prevent inadvertent displacement of the plunger-type stopper relative to the barrel, wherein the securing means is advantageously pivotally connected to the at least one support element, advantageously via at least one screw connection. Thus, the screw connection may prevent the securing device from pivoting in a fixed state and allow it to pivot in a released state. The securing device can also be equipped with an elastic element, such as a spring, so that the securing device automatically shifts from a release state, in which displacement of the plunger is permitted, to a securing state, in which displacement of the plunger is inhibited.

In an advantageous embodiment of the device, the device may comprise:
  a base plate;
  a support element connected to the base plate;
  a receptacle advantageously attached to the base plate comprising
    a first centering receptacle adapted to hold a second centering receptacle and advantageously having a depth stop, and
  the second centering receptacle, which is adapted to hold the syringe cylinder;
  a tubular barrel adapted to receive the plunger-type stopper therein;
  a holding device advantageously attached to the support element, which is adapted to hold the barrel relative to the receptacle and which advantageously at least partially encloses the barrel, wherein the holding device comprises a rocking device configured as an elongated plate-like element adapted to displace the barrel relative to the plunger-type stopper, wherein the rocking device advantageously has a first end adapted to be actuated by a finger and a second end arranged substantially opposite to the first end and at least partially enclosing the barrel; and
  a displacement device comprising a plunger guide adapted to align a plunger relative to the barrel, wherein the plunger guide is advantageously directly or indirectly adjustable;

the plunger which is adapted to displace the plunger-type stopper relative to the barrel and advantageously comprises a depth stop, and a plunger guide receptacle advantageously attached to the support element and adapted to hold the plunger guide; and optionally a securing means adapted to prevent inadvertent displacement of the plunger-type stopper relative to the barrel, wherein the securing means is advantageously pivotally connected to the at least one support element. With respect to this particular embodiment of the present invention, reference is made to the descriptions given for the corresponding individual features.

In a second aspect, the present invention relates to a method for manually inserting a plunger-type stopper of elastomer forming part of a plunger into a syringe cylinder in a fluid-tight manner, comprising the steps of:
  inserting the plunger-type stopper into a tubular barrel;
  inserting the syringe cylinder into a receptacle set up for this purpose;
  displacing the plunger-type stopper within the barrel to a predetermined position; and
  displacing the barrel relative to the plunger-type stopper by means of manual actuation of an actuation portion of a displacement device.

Already at this point it should be pointed out that all advantages, features and effects mentioned with respect to the device according to the invention are also applicable to the method according to the invention and vice versa.

Thus, also the method according to the invention allows to produce small series of syringes filled with a drug (and other syringe-like cylindrical tubes such as cartridges, double-chamber cartridges and double-chamber syringes) from a quantity of 1 while maintaining series conditions.

In this case, the plunger-type stopper can be arranged in the predetermined position inside the syringe cylinder. This means that the plunger-type stopper can be arranged in the predetermined position both inside the barrel and inside the syringe cylinder.

After the plunger-type stopper reaches the predetermined position within the barrel and syringe cylinder, the barrel may be displaced relative to the plunger-type stopper to a further position wherein the plunger-type stopper fully emerges from the barrel and expands to contact an inner surface of the syringe cylinder. In this way, the plunger-type stopper interacts with the syringe cylinder in a sealing manner.

The method according to the invention may further comprise the step of filling the syringe cylinder and optionally closing a syringe head before the syringe cylinder is inserted into the receptacle. This step of filling the syringe cylinder with a drug may be performed at a section of the device according to the invention set up for this purpose, or at a section separate from the device according to the invention. Filling can be carried out, for example, by means of a pipette or semi-automatic filling, advantageously in a sterile environment, such as in an isolator. According to the invention, it is possible to place all the equipment required for filling syringe cylinders on the one hand and for stoppering on the other hand in an isolator. This means that both filling and stoppering can be performed in a sterile environment.

Furthermore, the method may comprise the step of arranging the barrel in a holding device before the plunger-type stopper is inserted into the barrel. In this way, the holding device can be used to interchangeably connect different barrels.

The method may further comprise the step of displacing the receptacle with the syringe cylinder to a predetermined position prior to displacing the plunger-type stopper within the barrel, wherein the end of the barrel facing the syringe cylinder is at least partially within the syringe cylinder in the predetermined position of the syringe cylinder. In such an embodiment of the method according to the invention, the holding device may remain fixed with the barrel, for example relative to a frame to which the holding device is connected, whereas the syringe cylinder may be displaced to the predetermined position via the barrel.

The predetermined position of the receptacle with the syringe cylinder can be achieved by placing the receptacle against a depth stop mounted in the receptacle. This can prevent the syringe cylinder from being displaced beyond the predetermined position relative to the barrel, which in turn can prevent the barrel from coming into contact with the drug.

Prior to displacing the plunger-type stopper within the syringe cylinder, the receptacle with the syringe cylinder and the barrel can be adjusted so that they are substantially coaxial with each other. This allows the barrel and syringe cylinder to be moved relative to each other without contacting each other, which could contaminate an inner wall of the syringe cylinder, for example.

Further, the displacement of the plunger-type stopper within the barrel may be effected by a displacement device adapted to displace the plunger-type stopper relative to the barrel. In this case, a displacement direction of the displacement device may be substantially parallel or coaxial to a longitudinal center axis of the barrel and/or the syringe cylinder.

In particular, the displacement of the plunger-type stopper within the barrel can be effected by applying, advantageously manually, a compressive force to a plunger which forms part of the displacement device and which is adapted to displace the plunger-type stopper relative to the barrel. As already described with reference to the device according to the invention, the plunger can displace the plunger-type stopper through the barrel in particular in such a way that the plunger-type stopper maintains a desired orientation relative to the barrel, i.e., an unintentional tilting of the plunger-type stopper can be prevented.

In this case, the predetermined position of the plunger-type stopper can advantageously be achieved by arranging a depth stop arranged on the plunger against a plunger guide. Here, too, a depth stop can prevent the plunger-type stopper from being displaced beyond the predetermined position.

Advantageously, the displacement of the barrel relative to the plunger-type stopper can be effected by means of manually exerting an actuating force acting in a first direction, advantageously with a finger, on a first end of a rocking device, whereby a lever force acting in a second direction is transmitted to the barrel at a second end of the rocking device, which is arranged substantially opposite to the first end and which advantageously at least partially encloses the barrel, wherein the first direction is arranged substantially opposite to the second direction. This allows the barrel to be displaced out of its holding device such that it moves away from the syringe cylinder, releasing the plunger-type stopper so that it expands and comes into contact with the syringe cylinder. At the latest after removal of the finished syringe, the barrel can be displaced back to its original position in its holding device, for example due to gravity or due to a new plunger-type stopper being inserted into the barrel.

In this case, the displacement of the barrel relative to the plunger-type stopper can be achieved by means of (i) holding the plunger-type stopper in the predetermined position within the syringe cylinder by means of exerting a holding force on the plunger-type stopper, advantageously via a fixable plunger which constitutes part of the displacement device and which is adapted to displace the plunger-type stopper relative to the barrel and which advantageously rests against a plunger guide with a depth stop arranged thereon, and (ii) exerting a compressive force, advantageously with a finger, on a first end of an elongated plate-like element, thereby transmitting to the barrel, at a second end arranged opposite the first end and at least partially enclosing the barrel, a lever force whose direction is substantially opposite to the compressive force, so that the plunger-type stopper completely emerges from the barrel and expands in such a way that it comes into contact with an inner surface of the syringe cylinder. As mentioned above, a plunger-type stopper in a syringe cylinder can thus be brought close to a filling level of a drug arranged in the syringe cylinder without creating an overpressure in the syringe cylinder, which can, for example, expel drug from the syringe cylinder.

In an advantageous embodiment of the method according to the invention, the method may comprise the following steps of:

inserting the plunger-type stopper into a tubular barrel;

inserting an advantageously filled syringe cylinder into a receptacle adapted thereto comprising a first centering receptacle adapted to hold a second centering receptacle and the second centering receptacle adapted to hold the syringe cylinder;

displacing the second centering receptacle with the syringe cylinder to a predetermined position within the first centering receptacle, wherein the predetermined position is advantageously achieved by placing the second centering receptacle against a depth stop mounted in the first centering receptacle;

arranging the barrel with the plunger-type stopper in a holding device;

optionally, adjusting the receptacle with the syringe cylinder and the barrel so that they are aligned substantially coaxially with each other;

releasing a securing device which is arranged to prevent unintentional displacement of the plunger-type stopper relative to the barrel;

displacing the plunger-type stopper within the barrel by exerting, advantageously manually, a compressive force on a plunger adapted to displace the plunger-type stopper relative to the barrel, wherein the plunger-type stopper, which is arranged at the end of the plunger-type stopper opposite to the plunger, is displaced to a predetermined position by means of the compressive force exerted on the plunger, wherein the predetermined position of the plunger-type stopper is advantageously achieved by placing a depth stop arranged on the plunger against a plunger guide; and displacing the barrel relative to the plunger-type stopper by holding the plunger-type stopper in the predetermined position inside the syringe cylinder by exerting a holding force on the plunger-type stopper via the plunger, which advantageously rests against the plunger guide with the depth stop; and exerting a compressive force, advantageously with a finger, on a first end of an elongated plate-like element, whereby at a second end, which is arranged opposite to the first end and at least partially encloses the barrel, a lever force is transmitted to the barrel, the direction of which is substantially opposite to the compressive force, wherein the plunger-type stopper completely emerges from the barrel and expands such that it comes into contact with an inner surface of the syringe cylinder.

With reference to the above description of the method according to the invention and the device according to the invention concerning the individual features of this embodiment, this embodiment can represent a particularly simple realization for producing very small series of syringes filled with drugs, also of different syringe formats, while maintaining series conditions.

Figure 1:
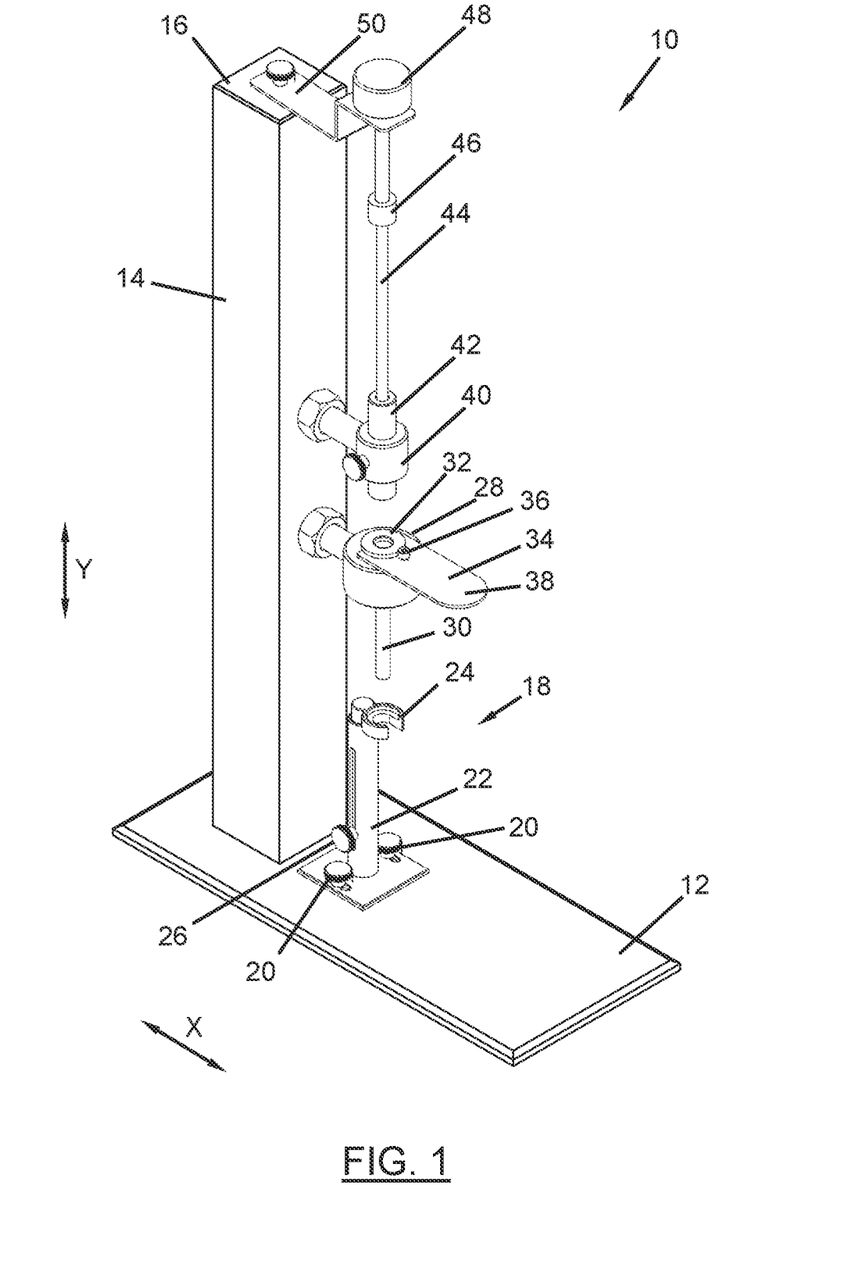
FIG. 1 shows a perspective view of an embodiment of a device according to an example embodiment of the invention.

In FIG. 1, an embodiment of the device according to the invention is generally designated by the reference sign 10. The device 10 comprises a base plate 12 as a bottom plate on which the device 10 stands. Connected to the base plate 12 is a support element 14, which is formed here as a square tube which is welded to a cover 16 at its end opposite the base plate 12.

A syringe receptacle 18 is also connected to the base plate 12 via two screws 20 in the embodiment shown in FIG. 1. The connection of the syringe receptacle 18 to the base plate 12 allows here a displacement of the syringe receptacle 18 along an axis X towards or away from the support element 14. The syringe receptacle 18 includes a first centering receptacle 22 adapted to receive a second centering receptacle 24, wherein the second centering receptacle 24 is in turn adapted to receive a syringe cylinder (not shown). The second centering receptacle 24 is displaceable in the first centering receptacle 22 along an axis Y, wherein a screw 26 connected to the second centering receptacle 24 and engaging the first centering receptacle 22 forms a depth stop 26 and allows adjustment of the two centering receptacles 22, 24 relative to each other in a desired position.

Along the direction Y, a holding device 28 is screwed to the support element 14 above the second centering receptacle 24 in such a way that the holding device 28 can be displaced along the axis X relative to the support element 14 when the screw connection is loosened. The holding device 28 has a central through-bore into which a barrel 30 is inserted. The barrel 30 includes a collar 32 at its end of the tube portion opposite the second centering receptacle 24, the collar 32 extending radially outwardly from the tube portion of the barrel 30. On the one hand, the collar 32 defines a predetermined position of the barrel 30 relative to the holding device 28. On the other hand, an actuation portion 34 engages with the collar 32 and at least partially surrounds the barrel 30 between the collar 32 and the holding device 28.

The actuation portion 34 is designed here as a plate-like rocking device, which is supported here on the holding device 28 via an adjusting screw 36, via which a pretension or an inclination of the actuation portion 34 relative to the holding device 28 or the barrel 30 can be adjusted, so that an actuation of the actuation portion 34 at its end 38 opposite to the barrel 30, for example by a finger pressure of a user, in the Y-direction in FIG. 1 downwards causes a lifting of the barrel 30 in the Y-direction in FIG. 1 upwards.

In the Y-direction in FIG. 1 above the holding device 28, a plunger guide receptacle 40 is connected to the support element 14, which is also displaceable and adjustable relative to the support element 14 along the X-axis. Connected to the plunger guide receptacle 40 is a plunger guide 42, in which a plunger 44 is displaceably arranged along the Y-direction. The section of the plunger 44 facing the barrel 30 has an outer diameter which is smaller than an inner diameter of the barrel 30, so that the plunger 44 can dip into the barrel 30. At a predetermined, in particular adjustable, position of the plunger 44, a depth stop 46 is connected thereto, which can come into contact with the plunger guide 42 in such a way that a displacement of the plunger in the Y-direction beyond a position defined by the depth stop 46 is prevented.

At its end opposite the barrel 30, the plunger 44 has a pressure head 48 which serves as a gripping surface for an operator. In FIG. 1, it can be seen that a securing device 50 is engaged with the print head 48, which prevents a displacement of the plunger 44, in particular from the position shown in FIG. 1 along the Y-direction downwards. The embodiment of the securing device 50 shown in FIG. 1 is adapted to be pivoted about the Y-axis to release displacement of the plunger 44.

In the following, the method according to the invention in one possible embodiment will be briefly described again with reference to the device 10 according to the invention. First, a plunger-type stopper is inserted into the barrel 30 using, for example, tweezers. Then, a syringe cylinder filled with a drug is inserted into the second centering receptacle 24. The second centering receptacle 24 is now displaced upward in the direction Y in FIG. 1 until further displacement is limited by the depth stop 26. In this position, the screw 26 is tightened so that the relative position of the second centering receptacle 24 to the first centering receptacle 22 is fixed. In this condition, the barrel 30 is immersed in the syringe cylinder. Next, the securing device 50 is pivoted to the side so that the plunger 44 can be displaced downward in the Y-direction until the depth stop 46 rests against the plunger guide 42. While an operator maintains a pressure on the plunger 48, the operator presses on the first end 38 of the actuation portion 34 in the Y-direction from top to bottom, at least partially displacing the barrel 30 upwardly out of the syringe cylinder. This releases the plunger-type stopper, which continues to be held in position relative to the syringe cylinder by the plunger 44, allowing it to expand to engage the syringe cylinder in a sealing manner.

Subsequently, the plunger 44 and the second centering receptacle 24 are moved back to their initial positions and the syringe cylinder provided with the plunger-type stopper can be removed from the device 10.

The following items are subject matter of the invention. It is noted that the following items may be combined in any order and in any combination or sub-combination with one another:

Example embodiments of the invention can be achieved by a device (10) for manually inserting a plunger-type stopper made of elastomer forming part of a plunger into a syringe cylinder, comprising:

a receptacle (18) adapted to hold the syringe cylinder;

a tubular barrel (30) adapted to receive the plunger-type stopper in its interior;

a holding device (28) adapted to hold the barrel (30) relative to the receptacle (18); and a displacement device (40, 42, 44, 46, 48) adapted to displace the plunger-type stopper relative to the barrel (30);

wherein the holding device (28) comprises an actuation portion (34) adapted to be manually actuated to displace the barrel (30) relative to the plunger-type stopper.

The device (10) can be characterized in that the actuation portion (34) of the holding device (28) comprises a rocking device (34) adapted to transfer a manual actuating force acting in a first direction, which has been input at a first end of the rocking device (34), into a lever force acting in a second direction at a second end of the rocking device (34) arranged opposite to the first end, wherein the first direction is substantially opposite to the second direction.

The device (10) can be characterized in that the rocking device (34) is designed as an elongated plate-like element.

The device (10) can be characterized in that the plate-like element (34) has a first end (38) adapted to be actuated by a finger and a second end disposed substantially opposite the first end (38) and which at least partially encloses the barrel (30).

The device (10) can be characterized in that it further comprises at least one support element (14) to which the holding device (28) and/or the displacement device (40, 42, 44, 46, 48) are/is connected.

The device (10) can be characterized in that it further comprises a base plate (12) advantageously connected to the at least one support element (14) according to item 5.

The device (10) can be characterized in that the receptacle (18) is attached to the base plate (12).

The device (10) can be characterized in that the receptacle (18) is adjustable relative to the holding device (28) and/or the displacement device (40, 42, 44, 46, 48), advantageously via at least one screw connection (26).

The device (10) can be characterized in that the holding device (28) and/or the displacement device (40, 42, 44, 46, 48) and/or the receptacle (18) can be adjusted relative to one another, advantageously by means of at least one screw connection (26) in each case.

The device (10) can be characterized in that the barrel (30) is further adapted to be displaceable relative to the receptacle (18) such that, in a predetermined position of its displacement path, it projects at least partially into an interior of a syringe cylinder arranged on the receptacle (18).

The device (10) can be characterized in that the barrel (30) has a radially outwardly extending collar (32) at one end.

The device (10) can be characterized in that the receptacle (18) arranged for holding the syringe cylinder comprises at least two parts.

The device (10) can be characterized in that the receptacle (18) comprises a first centering receptacle (22) adapted to hold a second centering receptacle (24) and the second centering receptacle (24) adapted to hold the syringe cylinder, wherein the second centering receptacle (24) dips at least partially into the first centering receptacle (22).

The device (10) can be characterized in that the first centering receptacle (22) has a depth stop (26) which is adapted to limit the displacement path of the second centering receptacle (24).

The device (10) can be characterized in that the second centering receptacle (24) has, at its end substantially opposite the first centering receptacle (22), a holder for a syringe cylinder, which is advantageously of hollow-cylindrical or clamp-like design.

The device (10) can be characterized in that the holding device (28) adapted to hold the barrel (30) at least partially encloses the barrel (30).

The device (10) can be characterized in that the holding device (28) is designed in the shape of a hollow cylinder with a bore, preferably concentric with the center axis of the holding device (28), for receiving (18) the barrel (30).

The device (10) can be characterized in that the displacement device (40, 42, 44, 46, 48) arranged to displace the plunger-type stopper relative to the barrel (30) comprises a plunger guide (42) adapted to align a plunger (44) relative to the barrel (30) and the plunger (44) adapted to displace the plunger-type stopper relative to the barrel (30).

The device (10) can be characterized in that the displacement device (40, 42, 44, 46, 48) further comprises a plunger guide receptacle (40) adapted to hold the plunger guide (42).

The device (10) can be characterized in that the plunger guide (42) or the plunger guide receptacle (40) are connected to the at least one support element (14), wherein the plunger guide (42) is advantageously adjustable directly or indirectly, advantageously via at least one screw connection.

The device (10) can be characterized in that the plunger (44) has a cylindrical portion at the end facing the holding device (28), the outer diameter of which is smaller than a clear inner diameter of the barrel (30).

The device (10) can be characterized in that the plunger (44) further comprises, at the end opposite the holding device (28), an advantageously radially outwardly extending head (48) adapted to be manually actuated, advantageously with a finger, to displace the plunger-type stopper relative to the barrel (30).

The device (10) can be characterized in that the plunger (44) further comprises an advantageously adjustable depth stop (46) adapted to define the end of the displacement path of the plunger-type stopper in the barrel (30) by the displacement device (40, 42, 44, 46, 48).

The device (10) can be characterized in that the device (10) further comprises a securing means (50) adapted to prevent inadvertent displacement of the plunger-type stopper relative to the barrel (30), wherein the securing device (50) is advantageously pivotally connected to the at least one support element (14), advantageously via at least one screw connection.

The device (10) can include a base plate (12); a support element (14) connected to the base plate (12); a receptacle (18) advantageously attached to the base plate (12), including a first centering receptacle (22) adapted to hold a second centering receptacle (24) and advantageously having a depth stop (26), and the second centering receptacle (24) adapted to hold the syringe cylinder, a tubular barrel (30) adapted to receive the plunger-type stopper in its interior; a holding device (28) advantageously attached to the support element (14), which is adapted to hold the barrel (30) relative to the receptacle (18) and which advantageously at least partially encloses the barrel (30), wherein the holding device (28) comprises a rocking device (34) configured as an elongated plate-like element, which is adapted to displace the barrel (30) relative to the plunger-type stopper, wherein the rocking device (34) advantageously has a first end (38) adapted to be actuated by a finger and a second end which is arranged substantially opposite the first end (38) and which at least partially encloses the barrel (30), and a displacement device (40, 42, 44, 46, 48) comprising a plunger guide (42) adapted to align a plunger (44) relative to the barrel (30), wherein the plunger guide (42) is advantageously directly or indirectly adjustable, the plunger (44) is adapted to displace the plunger-type stopper relative to the barrel (30) and advantageously comprises a depth stop (46), and a plunger guide receptacle (40) advantageously attached to the support element (14) and adapted to hold the plunger guide (42); and optionally a securing device (50) adapted to prevent inadvertent displacement of the plunger-type stopper relative to the barrel (30), wherein the securing device (50) is advantageously pivotally connected to the at least one support element (14).

Example embodiment of the present invention can include a method for manually inserting a plunger-type stopper made of elastomer forming part of a plunger into a syringe cylinder in a fluid-tight manner, comprising the steps of:

inserting the plunger-type stopper into a tubular barrel (30);

inserting the syringe cylinder into a receptacle (18) set up for this purpose;

displacing the plunger-type stopper within the barrel (30) to a predetermined position; and displacing the barrel (30) relative to the plunger-type stopper by means of manual actuation of an actuation portion (34) of a displacement device (40, 42, 44, 46, 48).

The method can be characterized in that the plunger-type stopper is arranged in the predetermined position inside the syringe cylinder.

The method can be characterized in that after the plunger-type stopper reaches the predetermined position within the barrel (30) and the syringe cylinder, the barrel (30) is displaced relative to the plunger-type stopper to a further position, wherein the plunger-type stopper fully emerges from the barrel (30) and expands such that it contacts an inner surface of the syringe cylinder.

The method can include the step of filling the syringe cylinder and optionally closing a syringe head before inserting the syringe cylinder into the receptacle (18).

The method can include the step of placing the barrel (30) in a holding device (28) before inserting the plunger-type stopper into the barrel (30).

The method can include the step of displacing the receptacle (18) with the syringe cylinder to a predetermined position prior to displacing the plunger-type stopper within the barrel (30), wherein the end of the barrel (30) facing the syringe cylinder is at least partially within the syringe cylinder in the predetermined position of the syringe cylinder.

The method can be characterized in that the predetermined position of the receptacle (18) with the syringe cylinder is achieved by placing the receptacle (18) against a depth stop (26) mounted in the receptacle (18).

The method can be characterized in that prior to displacing the plunger-type stopper within the barrel (30), the receptacle (18) with the syringe cylinder and the barrel (30) are adjusted to be substantially coaxially aligned.

The method can be characterized in that the displacement of the plunger-type stopper within the barrel (30) is effected by a displacement device (40, 42, 44, 46, 48) adapted to displace the plunger-type stopper relative to the barrel (30).

The method can be characterized in that the displacement of the plunger-type stopper within the barrel (30) is effected by exerting, advantageously manually, a compressive force on a plunger (44) which constitutes part of the displacement device (40, 42, 44, 46, 48) and which is adapted to displace the plunger-type stopper relative to the barrel (30).

The method can be characterized in that the predetermined position of the plunger-type stopper is advantageously achieved by arranging a depth stop (46) arranged on the plunger (44) against a plunger guide (42).

The method can be characterized in that the displacement of the barrel (30) relative to the plunger-type stopper is effected by means of manual exertion of an actuating force acting in a first direction, advantageously with a finger, on a first end (38) of a rocking device (34), as a result of which a lever force acting in a second direction is transmitted to the barrel (30) at a second end of the rocking device (34), which is arranged substantially opposite the first end (38) and which advantageously at least partially encloses the barrel (30), wherein the first direction is substantially opposite the second direction.

The method can be characterized in that the displacement of the barrel (30) relative to the plunger-type stopper is achieved by means of holding the plunger-type stopper in the predetermined position within the syringe cylinder by means of exerting a holding force on the plunger-type stopper, advantageously via a fixable plunger (44) which constitutes part of the displacement device (40, 42, 44, 46, 48) and which is adapted to displace the plunger-type stopper relative to the barrel (30) and which advantageously rests against a plunger guide (42) with a depth stop (46) arranged thereon, and exerting a compressive force, advantageously with a finger, on a first end (38) of an elongated plate-like element (34), thereby transmitting to the barrel (30), at a second end arranged opposite the first end (38) and at least partially surrounding the barrel (30), a lever force whose direction is substantially opposite to the compressive force, so that the plunger-type stopper emerges completely from the barrel (30) and expands so that it comes into contact with an inner surface of the syringe cylinder.

The method can be characterized in that the method comprises the following steps of:

inserting the plunger-type stopper into a tubular barrel (30);

inserting an advantageously filled syringe cylinder into a receptacle (18) adapted thereto comprising a first centering receptacle (22) adapted to hold a second centering receptacle (24) and the second centering receptacle (24) adapted to hold the syringe cylinder;

displacing the second centering receptacle (24) with the syringe cylinder to a predetermined position within the first centering receptacle (22), wherein the predetermined position is advantageously achieved by placing the second centering receptacle (24) against a depth stop (26) mounted in the first centering receptacle (22);

arranging the barrel (30) with the plunger-type stopper in a holding device (28);

optionally, adjusting the receptacle (18) with the syringe cylinder and the barrel (30) so that they are aligned substantially coaxially with each other;

releasing a securing device (50) adapted to prevent inadvertent displacement of the plunger-type stopper relative to the barrel (30);

displacing the plunger-type stopper within the barrel (30) by exerting, advantageously manually, a compressive force on a plunger (44) adapted to displace the plunger-type stopper relative to the barrel (30), wherein the plunger-type stopper, arranged at the end of the plunger-type stopper opposite to the plunger (44), is displaced to a predetermined position by means of the compressive force exerted on the plunger (44), wherein the predetermined position of the plunger-type stopper is advantageously achieved by placing a depth stop (46) arranged on the plunger (44) against a plunger guide (42); and displacing the barrel (30) relative to the plunger-type stopper by holding the plunger-type stopper in the predetermined position within the syringe cylinder by exerting a holding force on the plunger-type stopper via the plunger (44), which advantageously rests against the plunger guide (42) with the depth stop (46), and exerting a compressive force, advantageously with a finger, on a first end (38) of an elongated plate-like element (34), thereby transmitting to the barrel (30), at a second end arranged opposite the first end (38) and at least partially enclosing the barrel (30), a lever force whose direction is substantially opposite to the compressive force, wherein the plunger-type stopper completely emerges from the barrel (30) and expands to contact an inner surface of the syringe cylinder.

The invention claimed is:

1. Device (10) for manually inserting a plunger-type stopper made of elastomer forming part of a plunger into a syringe cylinder, comprising:
   receptacle (18) adapted to hold the syringe cylinder;
   a tubular barrel (30) adapted to receive the plunger-type stopper in its interior;
   a holding device (28) adapted to hold the barrel (30) relative to the receptacle (18); and
   a displacement device (40, 42, 44, 46, 48) adapted to displace the plunger-type stopper relative to the barrel (30);
   wherein the holding device (28) comprises an actuation portion (34) adapted to be manually operated to displace the barrel (30) relative to the plunger-type stopper,
   characterized in that the displacement device (40, 42, 44, 46, 48) adapted to displace the plunger-type stopper relative to the barrel (30) comprises a plunger guide (42) arranged to align a plunger (44) relative to the barrel (30), and the plunger (44) adapted to displace the plunger-type stopper relative to the barrel (30), wherein the plunger (44) comprises a cylindrical portion at the end facing the holding device (28), the outer diameter of which is smaller than a clear inner diameter of the barrel (30).

2. Device (10) according to claim 1, characterized in that the actuation portion (34) of the holding device (28) comprises a rocking device (34) advantageously designed as an elongated plate-like element, which is adapted to transfer a manual actuating force acting in a first direction, which has been input at a first end of the rocking device (34), into a lever force acting in a second direction at a second end of the rocking device (34) arranged opposite to the first end, the first direction being substantially opposite to the second direction.

3. Device (10) according to claim 1, characterized in that the holding device (28) or the displacement device (40, 42, 44, 46, 48) or the receptacle (18) are adjustable relative to one another, advantageously via at least one screw connection (26) in each case, and/or
   characterized in that the barrel (30) is further adapted to be displaceable relative to the receptacle (18) in such a way that, in a predetermined position of its displacement path, it projects at least partially into an interior space of a syringe cylinder arranged on the receptacle (18), and/or
   characterized in that the barrel (30) has a radially outwardly extending collar (32) at one end, and/or characterized in that the receptacle (18) arranged to hold the syringe cylinder comprises at least two parts.

4. Device (10) according to claim 1, characterized in that the holding device (28) set up for holding the barrel (30) at least partially encloses the barrel (30), wherein the holding device (28) is advantageously designed in the shape of a hollow cylinder with a bore, preferably concentric with the center axis of the holding device (28), for receiving (18) the barrel (30).

5. Device (10) according to claim 1,
   wherein the plunger (44) further comprises, at the end opposite the holding device (28), a radially outwardly extending head (48) which is adapted to be manually actuated to displace the plunger-type stopper relative to the barrel (30).

6. Device (10) according to claim 1, comprising:
   base plate (12);
   a support element (14) connected to the base plate (12);
   a receptacle (18) attached to the base plate (12), comprising
   a first centering receptacle (22) adapted to hold a second centering receptacle (24) and having a depth stop (26), and
   the second centering receptacle (24) adapted to hold the syringe cylinder;
   a tubular barrel (30) adapted to receive in its interior the plunger-type stopper;
   a holding device (28) attached to the support element (14), which is adapted to hold the barrel (30) relative to the receptacle (18) and which at least partially encloses the barrel (30), wherein the holding device (28) comprises a rocking device (34) configured as an elongated plate-like element, which is adapted to displace the barrel (30) relative to the plunger-type stopper, wherein the rocking device (34) has a first end (38) adapted to be actuated by a finger and a second end which is arranged substantially opposite the first end (38) and which at least partially encloses the barrel (30), and
   a displacement device (40, 42, 44, 46, 48) comprising
   a plunger guide (42) adapted to align a plunger (44) relative to the barrel (30), wherein the plunger guide (42) is directly or indirectly adjustable;
   the plunger (44) adapted to displace the plunger-type stopper relative to the barrel (30) and comprising a depth stop (46), and
   a plunger guide receptacle (40) attached to the support element (14) and adapted to hold the plunger guide (42); and
   a securing device (50) adapted to prevent inadvertent displacement of the plunger-type stopper relative to the barrel (30), wherein the securing device (50) is pivotally connected to the at least one support element (14).

7. Method for manually inserting a plunger-type stopper made of elastomer forming part of a plunger into a syringe cylinder in a fluid-tight manner, comprising the steps of:
   (i) inserting the plunger-type stopper into a tubular barrel (30);
   (ii) inserting the syringe cylinder into a receptacle (18) set up for this purpose;
   (iii) displacing the plunger-type stopper within the barrel (30) to a predetermined position; and
   (iv) displacing the barrel (30) relative to the plunger-type stopper by manual actuation of an actuation portion (34) of a displacement device (40, 42, 44, 46, 48), the displacement device (40, 42, 44, 46, 48) including a plunger guide (42) arranged to align a plunger (44) relative to the barrel (30), and the plunger (44) adapted to displace the plunger-type stopper relative to the barrel (30), wherein the plunger (44) comprises a cylindrical portion at the end facing the holding device (28), the outer diameter of which is smaller than a clear inner diameter of the barrel (30).

8. Method according to claim 7, characterized in that the displacement of the plunger-type stopper within the barrel (30) is effected by a displacement device (40, 42, 44, 46, 48) adapted to displace the plunger-type stopper relative to the barrel (30).

9. Method according to claim 7, characterized in that the displacement of the barrel (30) relative to the plunger-type stopper is effected by means of manual exertion of an actuating force acting in a first direction on a first end (38) of a rocking device (34), whereby at a second end of the rocking device (34), which is arranged opposite the first end (38) and which at least partially encloses the barrel (30), a lever force acting in a second direction is transmitted to the barrel (30), wherein the first direction is substantially opposite the second direction by (i) holding the plunger-type stopper in the predetermined position within the syringe cylinder by means of exerting a holding force on the plunger-type stopper via a fixable plunger (44) which constitutes part of the displacement device (40, 42, 44, 46, 48) and which is adapted to displace the plunger-type stopper relative to the setting barrel (30) and which rests against a plunger guide (42) with a depth stop (46) arranged thereon, and (ii) exerting a compressive force on a first end (38) of an elongated plate-like element (34), thereby transmitting to the barrel (30), at a second end arranged opposite the first end (38) and at least partially surrounding the barrel (30), a lever force whose direction is substantially opposite to the compressive force, so that the plunger-type stopper emerges completely from the barrel (30) and expands so that it comes into contact with an inner surface of the syringe cylinder.

10. Method according to claim 7, characterized in that the method comprises the following steps:

(i) inserting the plunger-type stopper into a tubular barrel (30);

(ii) inserting a filled syringe cylinder into a receptacle (18) adapted thereto comprising a first centering receptacle (22) adapted to hold a second centering receptacle (24) and the second centering receptacle (24) adapted to hold the syringe cylinder;

(iii) displacing the second centering receptacle (24) with the syringe cylinder to a predetermined position within the first centering receptacle (22), wherein the predetermined position is advantageously achieved by placing the second centering receptacle (24) against a depth stop (26) mounted in the first centering receptacle (22);

(iv) arranging the barrel (30) with the plunger-type stopper in a holding device (28);

(v) adjusting the receptacle (18) with the syringe cylinder and the barrel (30) so that they are aligned substantially coaxially with each other;

(vi) releasing a securing device (50) adapted to prevent inadvertent displacement of the plunger-type stopper relative to the barrel (30);

(vii) displacing the plunger-type stopper within the barrel (30) by exerting a compressive force on a plunger (44) adapted to displace the plunger-type stopper relative to the barrel (30), wherein the plunger-type stopper, arranged at the end of the plunger-type stopper opposite to the plunger (44), is displaced to a predetermined position by means of the compressive force exerted on the plunger (44), wherein the predetermined position of the plunger-type stopper is achieved by placing a depth stop (46) arranged on the plunger (44) against a plunger guide (42); and (viii) displacing the barrel (30) relative to the plunger-type stopper by holding the plunger-type stopper in the predetermined position within the syringe cylinder by exerting a holding force on the plunger-type stopper via the plunger (44), which rests against the plunger guide (42) with the depth stop (46); and exerting a compressive force on a first end (38) of an elongated plate-like element (34), thereby transmitting to the barrel (30), at a second end arranged opposite to the first end (38) and at least partially surrounding the barrel (30), a lever force whose direction is substantially opposite to the compressive force, wherein the plunger-type stopper completely emerges from the barrel (30) and expands to contact an inner surface of the syringe cylinder.

\* \* \* \* \*